United States Patent [19]
Leonard et al.

[11] Patent Number: 5,936,062
[45] Date of Patent: Aug. 10, 1999

[54] PROCESS FOR PREPARING CERTAIN AZA CYCLOHEXAPEPTIDES

[75] Inventors: William Leonard, Watchung; Kevin M. Belyk, Metuchen, both of N.J.

[73] Assignee: Merck & Co., Inc., Rahway, N.J.

[21] Appl. No.: 08/874,118

[22] Filed: Jun. 12, 1997

[51] Int. Cl.[6] ..................................................... C07K 7/00
[52] U.S. Cl. .......................... 530/317; 530/329; 530/338
[58] Field of Search ..................................... 530/338, 317, 530/329

[56] References Cited

U.S. PATENT DOCUMENTS

| | | | |
|---|---|---|---|
| 5,378,804 | 1/1995 | Balkovec et al. | 530/317 |
| 5,422,369 | 6/1995 | Stjernschantz et al. | 514/530 |
| 5,552,521 | 9/1996 | Belyk et al. | 530/317 |

FOREIGN PATENT DOCUMENTS

| | | |
|---|---|---|
| WO 94/21677 | 9/1994 | WIPO . |
| WO 94/25048 | 11/1994 | WIPO . |

OTHER PUBLICATIONS

Tetrahedron, vol. 49, No. 28, pp. 6195–6222 (1993), by Kurokawa, et al.

*Primary Examiner*—Cecilia J. Tsang
*Assistant Examiner*—C. Delacroix-Muirheid
*Attorney, Agent, or Firm*—Elliott Korsen; Mark R. Daniel

[57] ABSTRACT

There is disclosed a novel process for preparing aza cyclohexapeptides of the formula

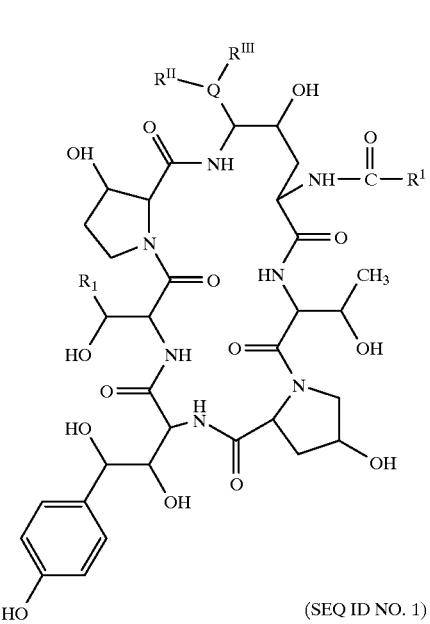

(I)

(SEQ ID NO. 1)

where all variables are defined herein.

15 Claims, No Drawings

```
                        SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 6 amino acids
        (B) TYPE: amino acid
        (C) STRANDEDNESS: unknown
        (D) TOPOLOGY: circular (ii) MOLECULE TYPE: peptide (iii) HYPOTHETICAL: NO (iv) ANTI-SENSE: NO (xi) SEQUENCE DESCRIPTION: SEQ ID NO:1:

Xaa Thr Xaa Xaa Xaa Xaa
1               5
```

PROCESS FOR PREPARING CERTAIN AZA CYCLOHEXAPEPTIDES

BACKGROUND OF THE INVENTION

This invention relates to an improved process for preparing certain aza cyclohexapeptides of the kind disclosed in U.S. Pat. No. 5,378,804 which issued Jan. 3, 1995. The initial process disclosed to synthesize these compounds required five steps and was not significantly stereoselective or high yielding. Known reductions of primary amides, such as hydrogenation, metal hydride and electrochemical reduction, require forcing conditions incompatible with the other amides and functional groups in the pneumocandin series. These reductions suffer from lack of chemoselectivity among differently substituted amides. An improved three step process was disclosed in copending application Ser. No. 08/386,618, however, this process has a maximum chemical yield in the range of about 23–25%. The new process described herein results in higher yields and easier synthesis of analogs of the compounds.

SUMMARY OF THE INVENTION

This invention is directed to a process for preparing aza cyclohexapeptides of the formula:

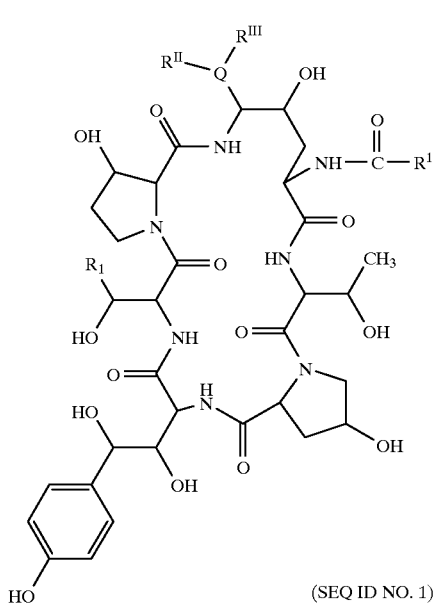

(I)

(SEQ ID NO. 1)

wherein
$R_1$ is $CH_2CH_2NH_2$ or $CH_2CONH_2$;
$R^I$ is $C_9$–$C_{21}$ alkyl,
   $C_9$–$C_{21}$ alkenyl,
   $C_1$–$C_{10}$ alkoxyphenyl,
   $C_1$–$C_{10}$ alkoxynaphthyl; or
   $C_1$–$C_{10}$ alkoxyterphenyl:
$R^{II}$ is H, $C_1$–$C_4$ alkyl,
   $C_3$–$C_4$ alkenyl,
   $(CH_2)_{2-4}OH$, or
   $(CH_2)_{2-4}NR^{IV}R^V$;
$R^{III}$ is H, $C_1$–$C_4$ alkyl $C_3$–$C_4$ alkenyl, $(CH_2)_{2-4}OH$, $(CH_2)_{2-4}NR^{IV}R^V$, or
$R^{II}$ and
$R^{III}$ taken together are $(CH_2)_4$, $(CH_2)_5$, $(CH_2)_2O(CH_2)_2$ or $(CH_2)_2NH(CH_2)_2$;
$R^{IV}$ is H or $C_1$–$C_4$ alkyl;

$R^V$ is H or $C_1$–$C_4$ alkyl;
Q is N or O; or
pharmaceutically acceptable acid addition salts thereof.

The compounds prepared by the process of this invention have been found to be useful in treating fungal infections especially those caused by Candida, Aspergillus, Histoplasma, Coccidioides and Blastomyces. They have also been found useful for the treatment and prevention of infections caused by *Pneumocystis carinii* which are often found in immunocompromised patients such as those with AIDS.

There are also disclosed novel intermediates useful in the process of the invention.

DETAILED DESCRIPTION OF THE INVENTION

This invention relates to a process for preparing compounds of formula (I) through a stereoselective, high yielding process.

Throughout the specification and appended claims, a given chemical formula or name shall encompass all optical and stereoisomers as well as racemic mixtures where such isomers and mixtures exist.

The term alkyl refers to straight, branched or cyclic chain hydrocarbon groups, e.g., methyl, ethyl, n-propyl, isopropyl, n-butyl, pentyl, hexyl, heptyl, cyclopentyl, cyclohexyl, cyclohexylmethyl and the like.

The term cycloalkyl refers to a species of alkyl containing from 3 to 15 carbon atoms without alternating or resonating double bonds between carbon atoms.

The term alkenyl refers to groups such as, e.g., vinyl, 1-propene-2-yl, 1-butene-4-yl, 2-buten-4-yl, 1-pentene-5-yl and the like.

The term alkoxy refers to straight or branched chain oxyalkyl groups such as, e.g., methoxy, ethoxy, butoxy, heptoxy, dodecyloxy, and the like.

The compounds of the present invention are generally obtained as mixtures of stereoisomeric forms in which one form usually predominates. Conditions may be adjusted by means within the normal skill of the skilled artisan to obtain predominantly the desired isomer. The compounds with preferred stereoisomeric form designated herein as the "normal" form are those in which the group at the "C-5-orn" position is below the plane at the said position. The designation "epi" has been employed for those compounds in which the group at the "C-5-orn" position is above the plane. The "C-5-orn" position is defined as the 5-carbon on the 4-hydroxy ornithine component.

The compounds of the present invention may be administered in the form of pharmaceutically acceptable salts. The term "pharmaceutically acceptable salt" is intended to include all acceptable salts. Examples of acid salts are hydrochloric, nitric, sulfuric, phosphoric, formic, acetic, trifluoroacetic, propionic, maleic, succinic, malonic, methane sulfonic and the like which can be used as a dosage form for modifying the solubility or hydrolysis characteristics or can be used in sustained release or prodrug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, and tetramethylammonium hydroxide. These salts may be prepared by standard procedures, e.g. by reacting a free acid with a suitable organic or inorganic base, or alternatively by reacting a free base with a suitable organic or inorganic acid.

Also, in the case of an acid (—COOH) or alcohol group being present, pharmaceutically acceptable esters can be employed, e.g. methyl, ethyl, butyl, acetate, maleate, pivaloyloxymethyl, and the like, and those esters known in the art for modifying solubility or hydrolysis characteristics for use as sustained release or prodrug formulations.

In a preferred embodiment, the process of this invention comprises the steps of reacting Compound II of the formula:

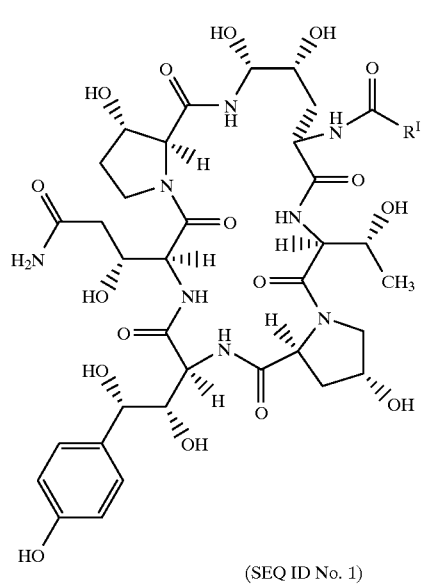

(II)

(SEQ ID No. 1)

with phenylboronic acid to afford Compound III of the formula:

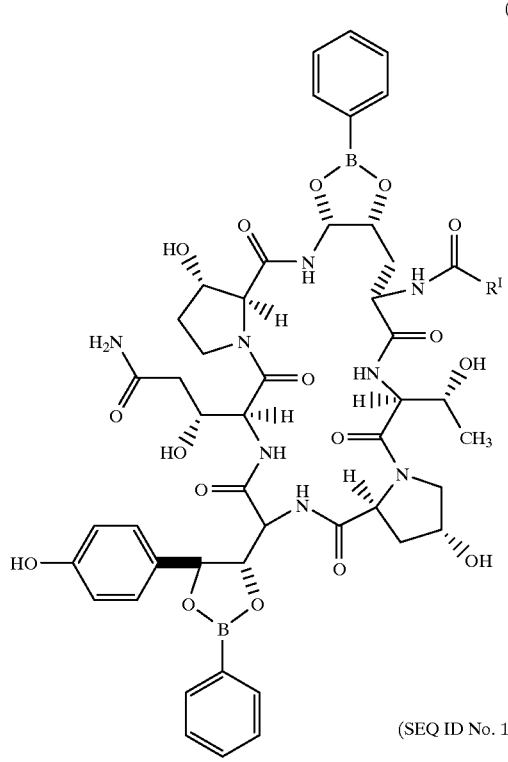

(III)

(SEQ ID No. 1)

which is subsequently reduced to the amine and then hydrolyzed to afford Compound IV of the formula:

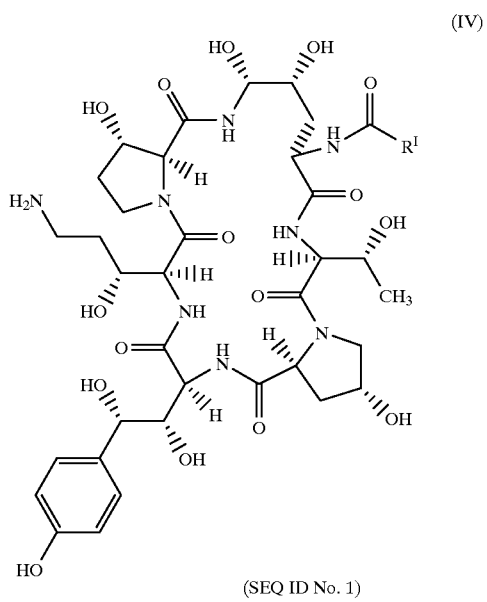

(IV)

(SEQ ID No. 1)

which is stereoselectively converted to Compound I through Compound V of the formula:

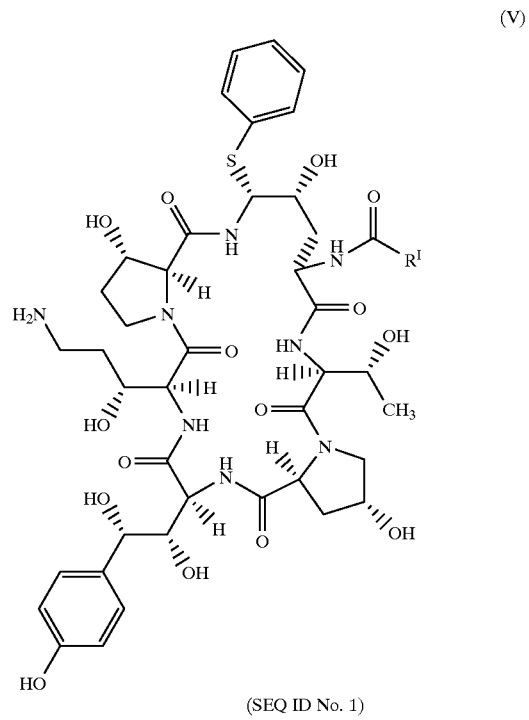

(V)

(SEQ ID No. 1)

by displacement of the phenylthio group.

In an alternative embodiment, the process comprises the steps of reacting Compound II of the formula:

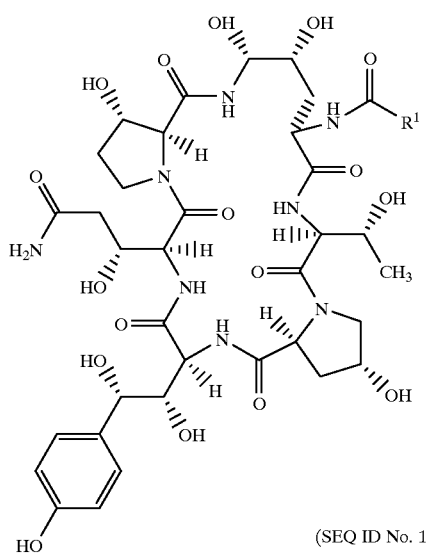
(II)
(SEQ ID No. 1)
with thiophenol to afford Compound VI of the formula:
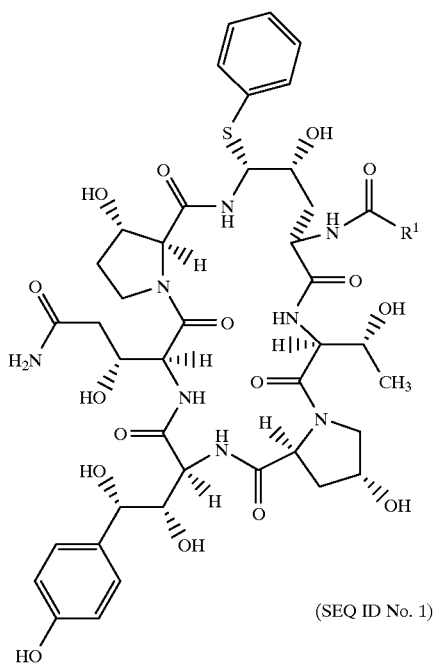
(VI)
(SEQ ID No. 1)
subsequently reacting Compound VI with phenylboronic acid to afford Compound IIIa of the formula:
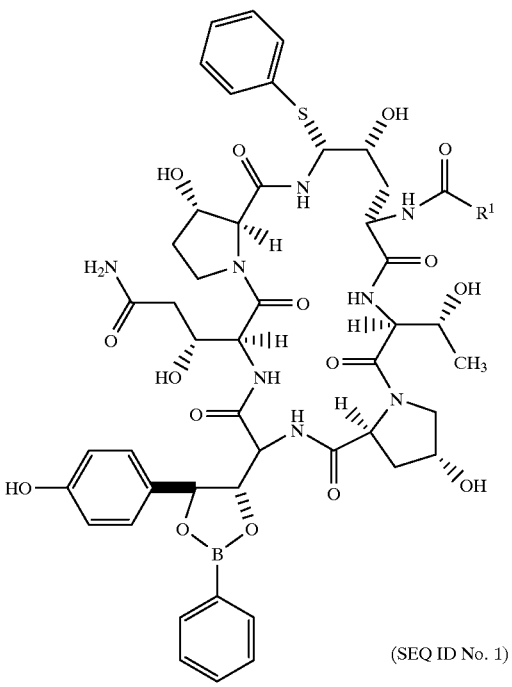
(IIIa)
(SEQ ID No. 1)
which is subsequently reduced to the amine and then hydrolyzed to afford Compound V of the formula:
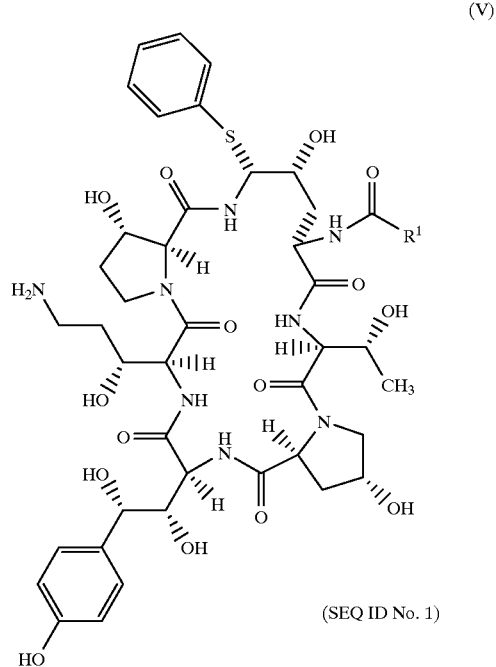
(V)
(SEQ ID No. 1)

which is stereoselectively converted to Compound I by displacement of the phenylthio group.

Compound II where $R^1$ is dimethyltridecyl, is disclosed and claimed in U.S. Pat. No. 5,202,309, which is incorporated herein by reference. Compound II can be produced by cultivating *Zalerion arboricola* ATCC 20868 in a nutrient medium enriched in mannitol as the primary source of carbon as described in U.S. Pat. No. 5,021,341, which is also incorporated herein by reference.

A preferred compound prepared by the process of the invention is shown below:

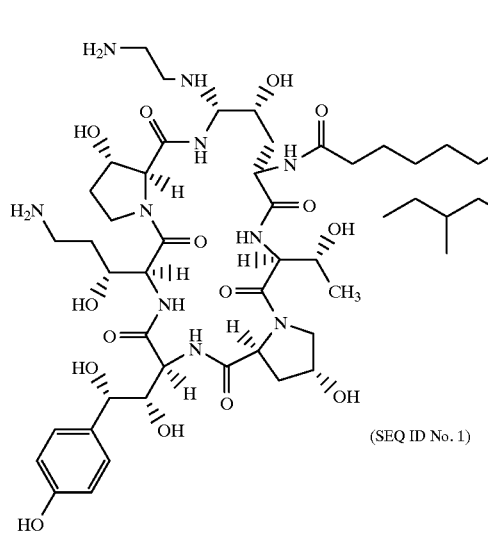

(Ia)

(SEQ ID No. 1)

A second preferred compound prepared by the process of the invention is shown below:

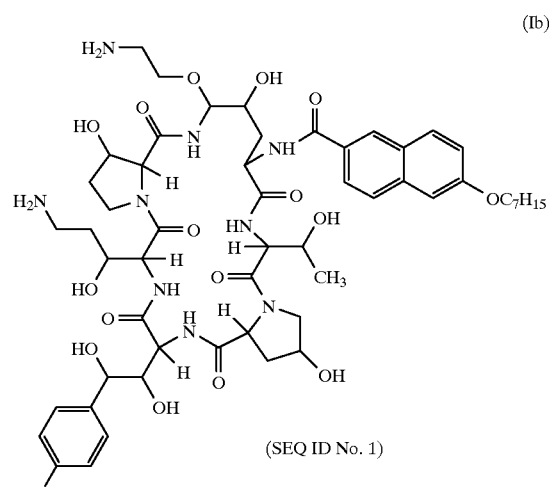

(Ib)

(SEQ ID No. 1)

The invention is illustrated in the following steps wherein preferred reactants are shown to more clearly demonstrate the process of the invention. $R'$ is dimethyltridecyl in the following reaction schemes.

REACTION SCHEME I

STEP 1

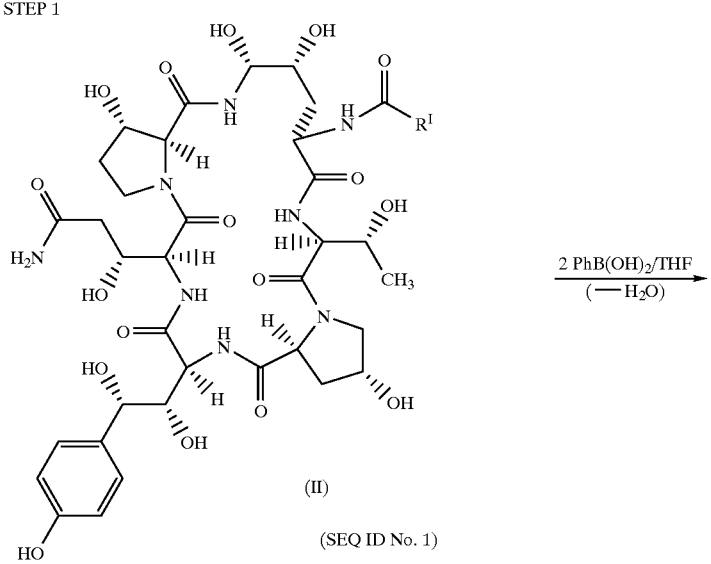

(II)

(SEQ ID No. 1)

2 PhB(OH)$_2$/THF
($-H_2O$)

STEP 2
-continued
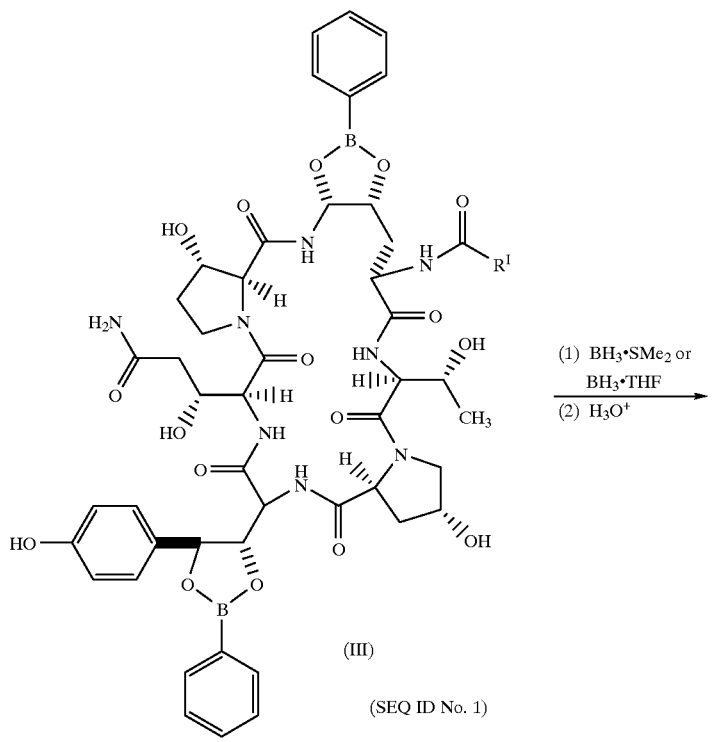
(III)
(SEQ ID No. 1)
(1) BH$_3$·SMe$_2$ or BH$_3$·THF
(2) H$_3$O$^+$
STEP 3
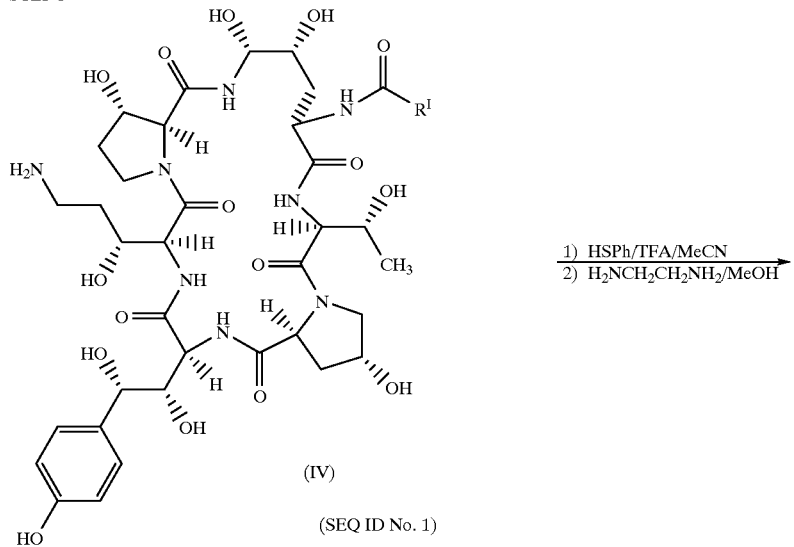
(IV)
(SEQ ID No. 1)
1) HSPh/TFA/MeCN
2) H$_2$NCH$_2$CH$_2$NH$_2$/MeOH

SCHEME I

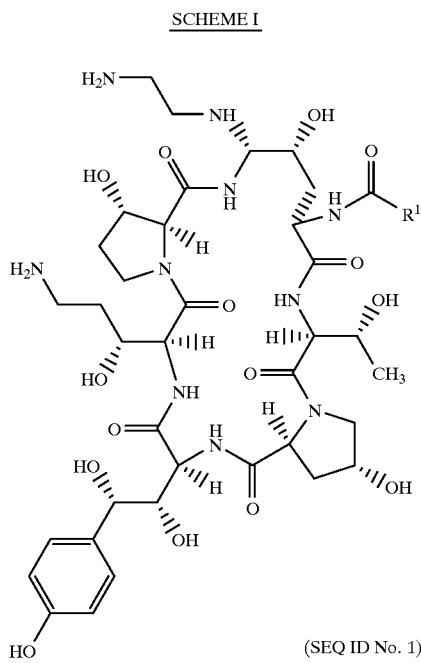

(Ia)

(SEQ ID No. 1)

As shown above, Step 1 involves the formation of the bis(phenylboronate) compound (Compound III) by reacting Compound II and dry THF with phenylboronic acid, p-methoxyphenylboronic acid or methaneboronic acid. 1–10 mole equivalents of the acid can be employed with 1–3 mole equivalents preferred.

Step 2 involves the reduction of Compound III to the amine (Compound IV) using a borane complex such as borane with tetrahydrofuran (THF), dimethylsulfide, diphenylsulfide, dibenzylsulfide, 1,4-oxathiane or $BH_2Cl$ with dimethylsulfide or a metal boride such as $ZrCl_4/NaBH_4$ or $TiCl_4/NaBH_4$ in THF or other suitable solvent. The reduction may also be carried out using borane complexes with ammonia, dimethylamine, pyridine or piperazine. Preferred reduction agents include the borane complexes with tetrahydrofuran (THF), dimethylsulfide, diphenylsulfide, dibenzylsulfide, 1,4-oxathiane or $BH_2Cl$ with dimethylsulfide or a metal boride such as $ZrCl_4/NaBH_4$ or $TiCl_4/NaBH_4$ in THF or other suitable solvent. Any amide unconverted by this reduction is separated using reverse phase chromatography. Following the reduction, Step 2 also involves the removal of the phenylboronate groups during workup with aqueous acid.

Step 3 involves two parts. First of all, the reaction of Compound IV with thiophenol in acetonitrile and trifluoroacetic acid (TFA) to produce a phenylsulfide containing intermediate. Any moderate strength acid is expected to produce the intermediate in good yield. Examples of such moderate strength acids include, but are not limited to, trifluoroacetic acid, phosphoric acid and trichloroacetic acid. Other sulfides such as 4-methoxythiophenol, 2-mercapto-1-methylimidazole and 2-mercaptobenzimidazole may be employed. Compound III is extracted by application of the diluted reaction solution to a reverse phase C-18 column, followed by elution with methanol.

The amount of TFA used is crucial to the rate of displacement as well as to the subsequent formation of the undesired sulfide at the homotyrosine segment of the cyclic peptide. It was found that from about 5% to about 25% TFA in acetonitrile gave the best yield and process aging time. The preferred TFA range was found to be from about 7% to about 15%.

The amount of thiophenol used in this step is also critical to the yield of the final product. 3 to 5 equivalents of the thiophenol provided the best yield.

The preferred conditions for the sulfide formation were determined to be 5 equivalents thiophenol in 10% TFA/acetonitrile at 0° C. These conditions resulted in a yield of 65–70% after solid phase extraction.

The second part of Step 3 involves the displacement of the phenylthio group. The phenylsulfide is reacted in neat ethylenediamine (1:3) at ambient temperature to provide Compound Ia in 95% yield. The reaction may take place at a temperature of about 10° C. to about 40° C. for about 0.5 to about 6.0 hours. Preferably the reaction takes place at room temperature for about 1.5 hours. The reaction can also be conducted using ethylenediamine dissolved in a suitable solvent such as water, methanol, ethanol, isopropanol, tetrahydrofuran, trifluoroethanol, dichloroethane or acetonitrile.

REACTION SCHEME II

STEP 1

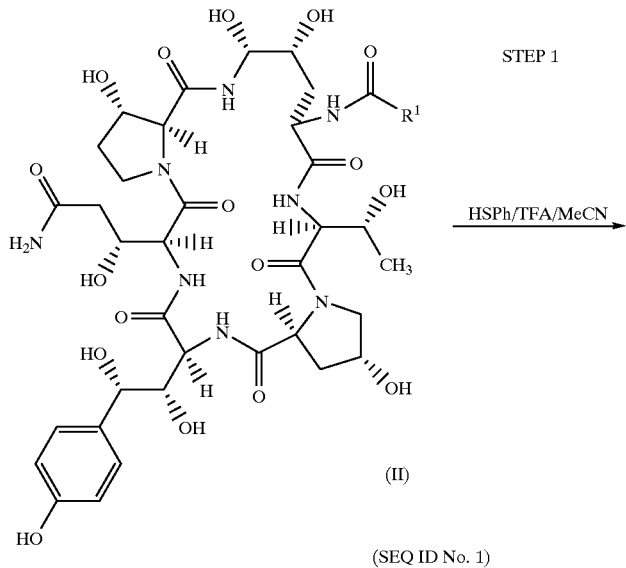

HSPh/TFA/MeCN (II)

(SEQ ID No. 1)

-continued
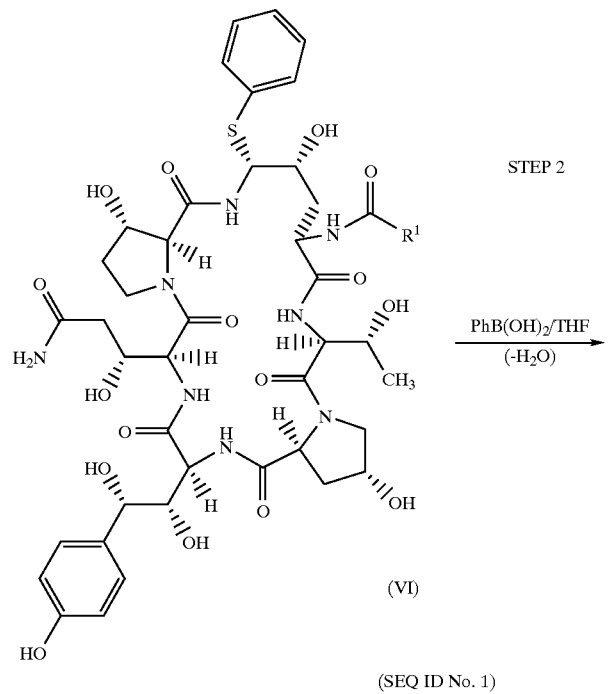
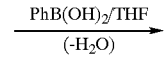
(VI)
(SEQ ID No. 1)
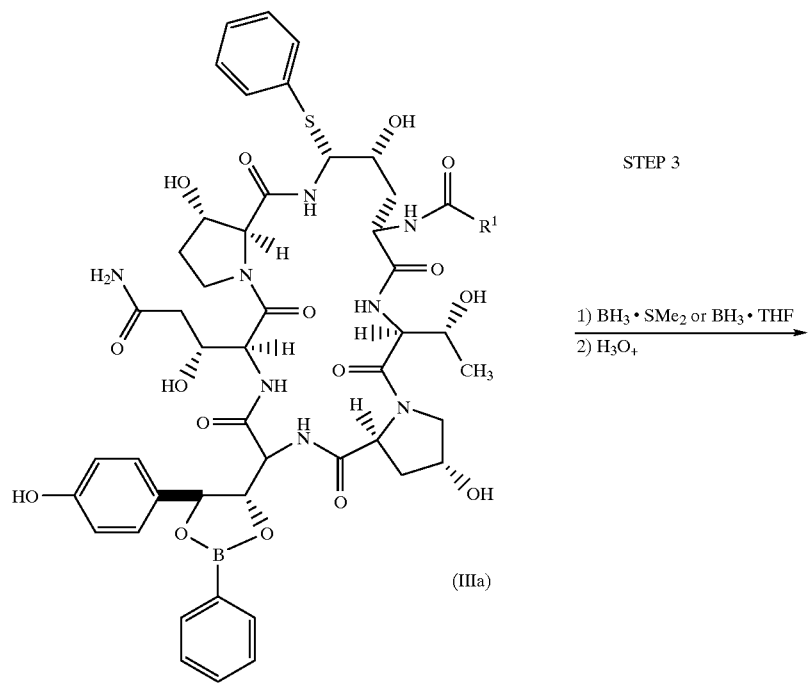
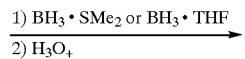
(IIIa)
(SEQ ID No. 1)

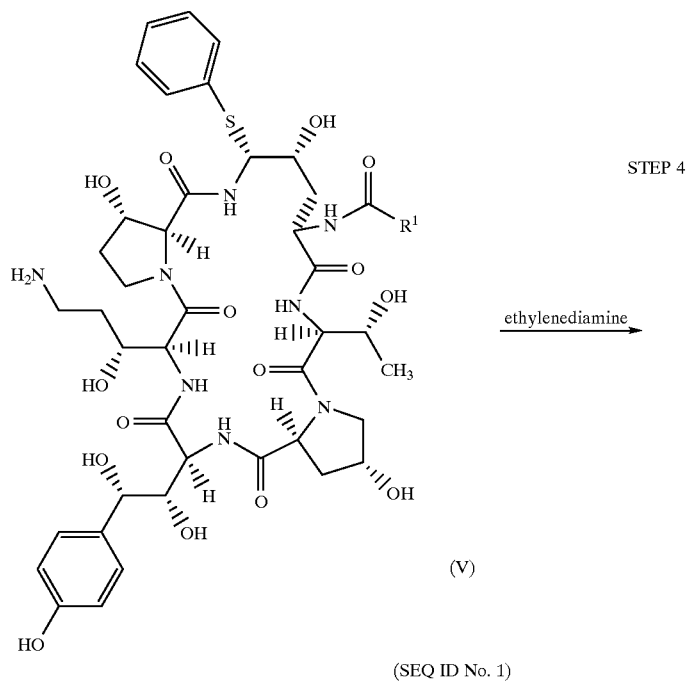

(V)

(SEQ ID No. 1)

SCHEME II

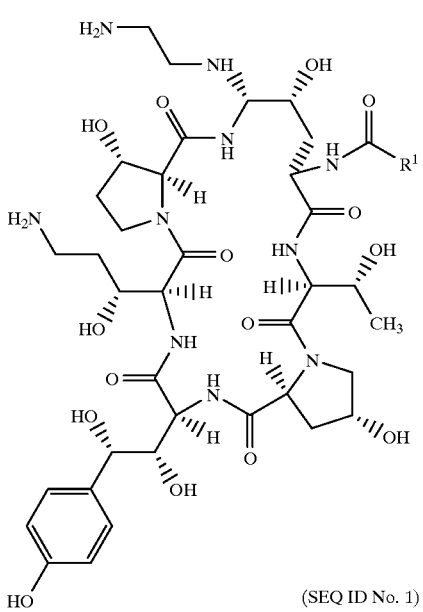

(Ia)

(SEQ ID No. 1)

As shown above, Step 1 involves the reaction of Compound II with thiophenol in acetonitrile and trifluoroacetic acid (TFA) to produce a phenylsulfide containing intermediate. Any moderate strength acid is expected to produce the intermediate in good yield. Examples of such moderate strength acids include, but are not limited to, trifluoroacetic acid, phosphoric acid and trichloroacetic acid. Other sulfides such as 4-methoxythiophenol, 2-mercapto-1-methylimidazole and 2-mercaptobenzimidazole may be employed. Compound VI is precipitated by addition of water and isolated by filtration.

The amount of TFA used is crucial to the rate of displacement as well as to the subsequent formation of the undesired sulfide at the homotyrosine segment of the cyclic peptide. It was found that from about 5% to about 25% TFA in acetonitrile gave the best yield and process aging time with a preferred TFA range of from about 7% to about 15%.

The amount of thiophenol used in this step is also critical to the yield of the final product. 3 to 5 equivalents of thiophenol provided the best yield.

The preferred conditions for the sulfide formation were determined to be 5 equivalents thiophenol in 10% TFA/acetonitrile at 0° C. These conditions resulted in a yield of 65–70% after solid phase extraction.

Step 2 involves the derivatization of the phenylsulfide containing intermediate by reacting it with phenylboronic acid, p-methoxyphenylboronic acid or methaneboronic acid in THF. 1–10 mole equivalents of the acid can be employed with 1–3 mole equivalents preferred.

Step 3 involves the reduction of Compound IIIa to the amine (Compound V) using a borane complex such as borane with tetrahydrofuran (THF), dimethylsulfide, diphenylsulfide, dibenzylsulfide, 1,4-oxathiane or $BH_2Cl$ with dimethylsulfide or a metal boride such as $ZrCl_4/NaBH_4$ or $TiCl_4/NaBH_4$ in THF or other suitable solvent. The reduction may also be carried out using borane complexes with ammonia, dimethylamine, pyridine or piperazine. Preferred reduction agents include the borane complexes with tetrahydrofuran (THF), dimethylsulfide, diphenylsulfide, dibenzylsulfide, 1,4-oxathiane or $BH_2Cl$ with dimethylsulfide or a metal boride such as $ZrCl_4/NaBH_4$ or $TiCl_4/NaBH_4$ in THF or other suitable solvent. Any amide unconverted by this reduction is separated using reverse phase chromatography.

Step 3 also involves the removal of the phenylboronate group during workup with aqueous acid.

Finally, Step 4 involves the displacement of the phenylthio group. The phenylsulfide is reacted in neat ethylenediamine (1:3) at ambient temperature to provide Compound Ia in 95% yield. The reaction may take place at a temperature of about 10° C. to about 40° C. for about 0.5 to about 6.0 hours. Preferably the reaction takes place at room temperature for about 1.5 hours. The reaction can also be conducted using ethylenediamine dissolved in a suitable solvent such as water, methanol, ethanol, isopropanol, tetrahydrofuran, trifluoroethanol, dichloroethane or acetonitrile.

Compounds III, IIIa, V and VI are novel intermediates which are useful in the process of the invention.

The invention is described in greater detail in the following examples in which all parts, preparations, ratios and percentages are by weight unless otherwise indicated. In the example, $R^I$ was dimethyltridecyl.

EXAMPLE 1 a) The Synthesis of Compound IV from Compound II (through Compound III)

Compound II (60 g gross, 52.6 g HPLC assay, 49.4 mmol) was added to dry THF (1480 mL). The $PhB(OH)_2$ (14.56 g, 119 mmol) was added to the suspension. The suspension was aged at room temperature then heated to reflux. During the room temperature aging and reflux, the reaction solution becomes homogeneous. The reflux condensate was passed through 3A molecular sieves in a liquid/solid extraction apparatus so as to dry the solution to less than 25 mol % water to Compound II. The reaction mixture was cooled to ambient temperature and diluted with 490 mL dry THF. The bis(phenylboronate) solution prepared above was cooled to about −7° C. and $BH_3.S(CH_3)_2$ (10 M, 33.3 mL, 6.7 mol equiv.) was added. The reaction was maintained at −12 to 0° C. and aged 6.5 hrs whereupon aq. HCl (2M, 140 mL, 280 mmol) was added slowly. HPLC assay indicated a 61% yield of Compound IV.

A portion of the quenched solution was diluted with water to a 1:5.7 v/v THF/water solution. This solution was loaded onto a medium-pressure liquid chromatography column of reverse-phase C-18 adsorbent. After loading, the compound IV was eluted with solutions of 1:4 v/v acetonitrile/water and then 1:3 v/v acetonitrile water.

The rich cuts (>80 HPLC area %) were combined and diluted with water to a 1:7.3 v/v acetonitrile/water solution. This mixture was loaded to the same column described above, and the column was eluted with methanol. The rich cut fractions (>85 HPLC area %) were combined and concentrated to give a typical recovery of 88–92% of Compound IV for the chromatography and isolation.

b) The Preparation of the Phenylsulfide (Compound V)

Compound IV (5.80 g assay, 0.00533 mol) was charged to 0.23 L of dry acetonitrile and cooled to −5° C. at which point thiophenol (3.10 g, 0.028 mol) was added. TFA (36 g, 24.5 mL, 0.318 mol) was added over 20 minutes in order to keep the temperature of the reaction mixture below 0° C. The reaction was aged at −10° to 0° C. until HPLC analysis showed <3 area % starting material (3.75 h). At this time, chilled water (0.56 L) was added slowly (1 h) while cooling the reaction mixture to maintain the temperature below 5° C. The assay yield of the α- and β-phenylsulfide adduct as the trifluoroacetate salt was 4.82 g (71%).

This solution was loaded on the same column described in step a and the column was washed with water (0.57 L), then the adsorbed organic compounds were eluted with methanol (0.50 L). The rich cuts were concentrated by rotary evaporation and static high vacuum. This yielded 7.20 g (57 wt % pure, 5.1 wt % water) of crude phenylsulfide trifluroacetate salt as an amorphous foamy solid. The corrected isolated step yield for the phenylsulfide was 4.10 g (61%) as a 93:7 mixture of the α- and β-aminal diastereomers.

c) Conversion of the Phenylsulfide to Compound Ia

The crude phenylsulfide trifluoromethanesulfonate salt (8.4 g crude, 57 wt % pure, 0.00377 mole) was added to ethylenediamine (24 mL) while stirring at ambient temperature. The resulting solution was stirred 1.5 h to complete the displacement, then methanol (40 mL) was added followed by acetic acid (45 mL), keeping the temperature below 25° C. with ice-bath cooling. A thick slurry resulted. Water (160 mL) was added to dissolve the slurry, and the aqueous layer was extracted by gentle shaking with hexanes (75 mL). The hexanes layer was back-extracted with water (40 mL) and the combined aq. layer was filtered through a medium-porosity sintered glass funnel, then purified by prep HPLC using a 50 mm diameter C18 column, using 22% acetonitrile/78% 0.15% aq. acetic acid as eluent. The rich cut was lyophilized to provide 4.2 g of 85 wt % pure Compound I-1 as the diacetate salt in 78% isolated step yield.

d) Crystallization of Compound Ia

The solid (2.3 g) was dissolved in ethanol (25 mL) and water (2.7 mL) was then added. The solution was passed through a sintered glass funnel to remove extraneous matter. To this filtrate was added acetic acid (0.14 mL) followed by the slow addition (1.75 h) of ethyl acetate (14 mL). The solution was seeded and the seed bed was aged for 1 h. The remaining ethyl acetate (32 mL) was added over 5 h and aged an additional 1 h. The crystalline solid was collected on a sintered-glass funnel and washed with a solution of ethanol/ethyl acetate/water (6 mL/9 mL/0.5 mL, respectively). The wet cake was dried with a nitrogen flow to give 1.91 g (1.75 assay g, 88% recovery) of the diacetate salt of compound Ia.

EXAMPLE 2 a) The Preparation of the Phenylsulfide (Compound VI)

Compound II (2.48 kg assay, 2.33 mol) was charged to 78 L of dry acetonitrile and cooled to −8° C. at which point thiophenol (1.08 kg, 9.8 mol) was added. TFA (12.8 kg, 8.65 L, 112 mol) was added over 30 minutes in order to keep the temperature of the reaction mixture below 0° C. The reaction was aged at −13° to 0° C. until HPLC analysis showed <3 area % starting material (5 h). At this time, chilled water (35 L) was added slowly while cooling the reaction mixture to maintain the temperature below 5° C. The product VI precipitates during water addition. Additional water was added to adjust the mixture to 1:3 v/v acetonitrile/water. The solids were removed by filtration and washed with 1:3 v/v acetonitrile/water until the pH of the filtrate was >pH5. The solid was dried under a nitrogen flow. The assay yield of Compound VI as the trifluoroacetate salt was 2.03 kg (76%).

b) The Synthesis of Compound V from Compound VI (Through Compound IIIa)

Compound VI (922 g assay, 0.94 mol) was added to dry THF (44 L). The $PhB(OH)_2$ (119 g, 0.98 mol) was added to the suspension. The suspension was aged at room temperature for 12 hours, then heated to reflux. The reflux condensate was passed through 3A molecular sieves in a liquid/solid extraction apparatus so as to dry the solution to less than 25 mol % water to Compound VI. The reaction mixture was cooled and additional dry THF was added to reconstitute the mixture to the original volume. The mixture was cooled to <-4° C. Neat BH$_3$.SMe$_2$ (494 g, 6.51 mol) was added over 15 minutes and the reaction mixture was maintained at -4 to 0° C. The reaction progress was monitored by HPLC until <30% of the starting material remaind, indicating the end of the reaction age (9 hours).

The mixture was cooled to -10° C. and slowly quenched with 2N HCl (2.98 L). The assay yield of Compound V as the hydrochloride salt was 573 g (61%).

The quenched solution was diluted to 1:3.76 v/v THF/water and loaded onto a medium-pressure column of RP-C18 adsorbent (16.8 kg). After loading, the column was eluted with 1:2.64 v/v acetonitrile/water, and then 1:2.45 v/v acetonitrile/water. The rich cuts (>80 HPLC area %) were combined to give a 90% yield of Compound V.

The combined rich cuts were diluted with water to a 1:2 v/v acetonitrile/water solution. This mixture was combined with the diluted rich cuts of a similar size reduction batch and loaded to the same column described above. The desired compound V was eluted with methanol. The rich cut fractions (>85 area %) were combined and concentrated by rotary evaporation to give a 98% recovery of Compound V.

Compound V was converted to Compound Ia as described above in Examples 1c and 1d.

What is claimed is:

1. A process for preparing aza cyclohexapeptide compounds of the formula

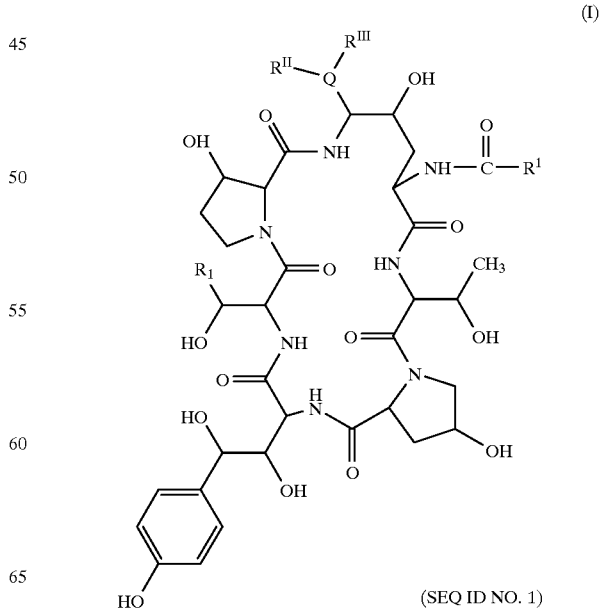

(SEQ ID NO. 1)

wherein $R_1$ is $CH_2CH_2NH_2$;

$R^I$ is $C_9$–$C_{21}$ alkyl,
  $C_9$–$C_{21}$ alkenyl,
  $C_1$–$C_{10}$ alkoxyphenyl,
  $C_1$–$C_{10}$ alkoxynaphthyl, or
  $C_1$–$C_{10}$ alkoxyterphenyl:

$R^{II}$ is H, $C_1$–$C_4$ alkyl,
  $C_3$–$C_4$ alkenyl,
  $(CH_2)_{2-4}OH$, or
  $(CH_2)_{2-4}NR^{IV}R^V$;

$R^{III}$ is H, $C_1$–$C_4$ alkyl $C_3$–$C_4$ alkenyl, $(CH_2)_{2-4}OH$, $(CH_2)_{2-4}NR^{IV}R^V$, or $R^{II}$ and $R^{III}$ taken together are $(CH_2)_4$, $(CH_2)_5$, $(CH_2)_2O(CH_2)_2$ or $(CH_2)_2NH(CH_2)_2$;

$R^{IV}$ is H or $C_1$–$C_4$ alkyl;

$R^V$ is H or $C_1$–$C_4$ alkyl;

Q is N or O; or pharmaceutically acceptable acid addition salts thereof which comprises the steps of a) reacting Compound II of the formula:

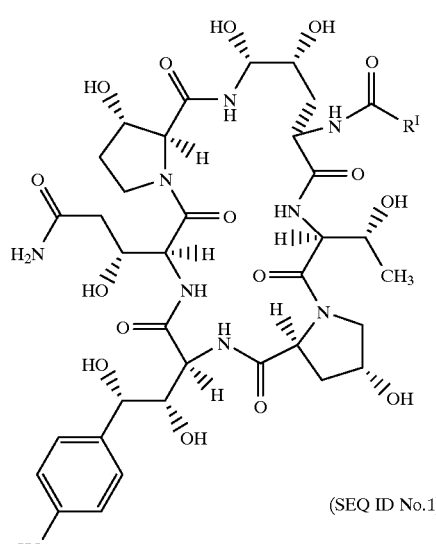

(II)

(SEQ ID No.1)

with phenylboronic acid, p-methoxyphenylboronic acid or methaneboronic acid to afford Compound III of the formula:

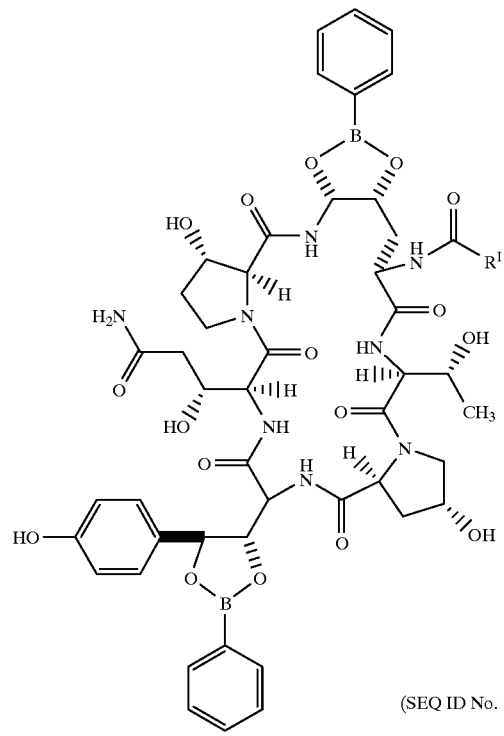

(III)

(SEQ ID No. 1)

b) which is subsequently reduced and hydrolyzed to afford Compound IV of the formula:

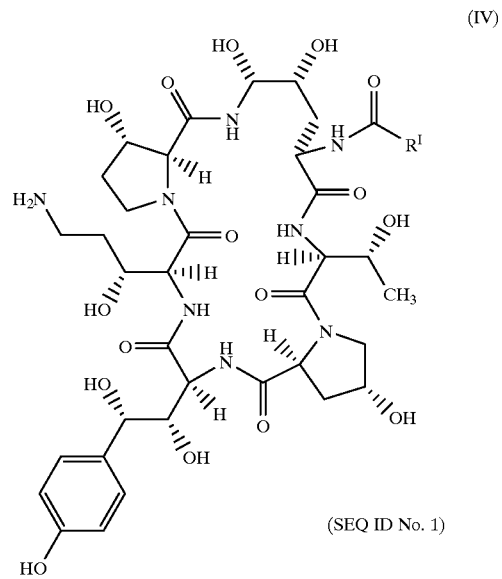

(IV)

(SEQ ID No. 1)

c) which is reacted with thiophenol in a suitable solvent to afford Compound V of the formula;

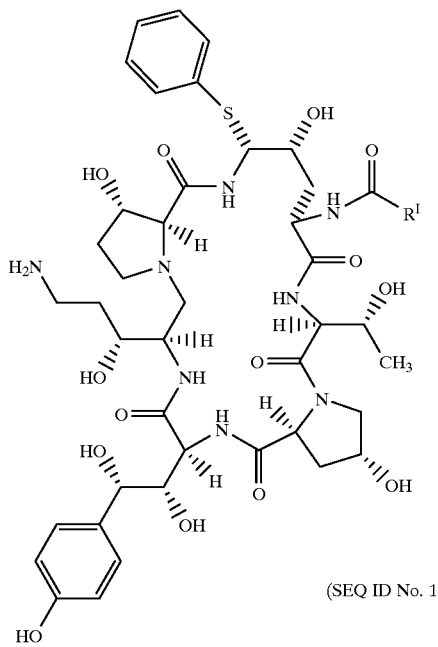

(V)

(SEQ ID No. 1)

which is stereoselectively converted to Compound I of the formula

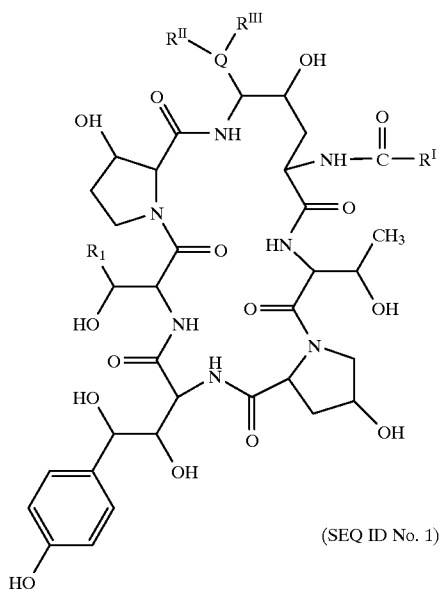

(I)

(SEQ ID No. 1)

by displacement of the phenylthio group.

2. The process of claim 1 wherein the reduction in Step (b) is accomplished using a borane complex or metal boride.

3. The process of claim 2 wherein the metal boride is $ZrCl_4/NaBH_4$ or $TiCl_4/NaBH_4$ and the borane complex is borane complexed with dimethylsulfide, dibenzylsulfide, diphenylsulfide, THF or 1,4-oxathiane or $BH_2Cl$ with dimethylsulfide.

4. The process of claim 1 wherein the suitable solvent in Step (c) is acetonitrile.

5. The process of claim 1 where the displacement of the phenylthio group takes place in neat ethylenediamine or with ethylenediamine dissolved in a suitable solvent at a temperature of about 10° C. to about 40° C.

6. The process of claim 5 wherein the suitable solvent is selected from the group consisting of water, methanol, ethanol, tetrahydrofuran, isopropanol, trifluoroethanol, acetonitrile and dichloromethane.

7. A process for preparing aza cyclohexapeptide compounds of the formula

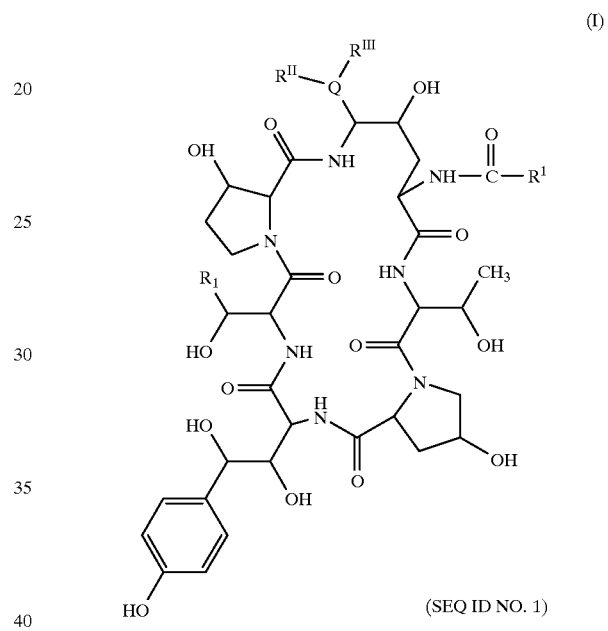

(I)

(SEQ ID NO. 1)

wherein $R_1$ is $CH_2CH_2NH_2$;

$R^I$ is $C_9$–$C_{21}$ alkyl,
$C_9$–$C_{21}$ alkenyl,
$C_1$–$C_{10}$ alkoxyphenyl,
$C_1$–$C_{10}$ alkoxynaphthyl, or
$C_1$–$C_{10}$ alkoxyterphenyl:

$R^{II}$ is H, $C_1$–$C_4$ alkyl,
$C_3$–$C_4$ alkenyl,
$(CH_2)_{2-4}OH$, or
$(CH_2)_{2-4}NR^{IV}R^V$;

$R^{III}$ is H, $C_1$–$C_4$ alkyl $C_3$–$C_4$ alkenyl, $(CH_2)_{2-4}OH$, $(CH_2)_{2-4}NR^{IV}R^V$, or $R^{II}$ and
$R^{III}$ taken together are $(CH_2)_4$, $(CH_2)_5$, $(CH_2)_2O(CH_2)_2$ or $(CH_2)_2NH(CH_2)_2$;

$R^{IV}$ is H or $C_1$–$C_4$ alkyl;

$R^V$ is H or $C_1$–$C_4$ alkyl; or pharmaceutically acceptable acid addition salts thereof which comprises the steps of a) reacting Compound II of the formula

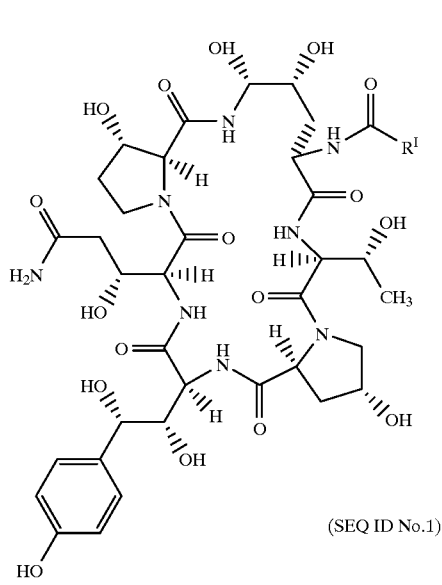
(II)
(SEQ ID No.1)

with thiophenol to afford Compound VI of the formula:

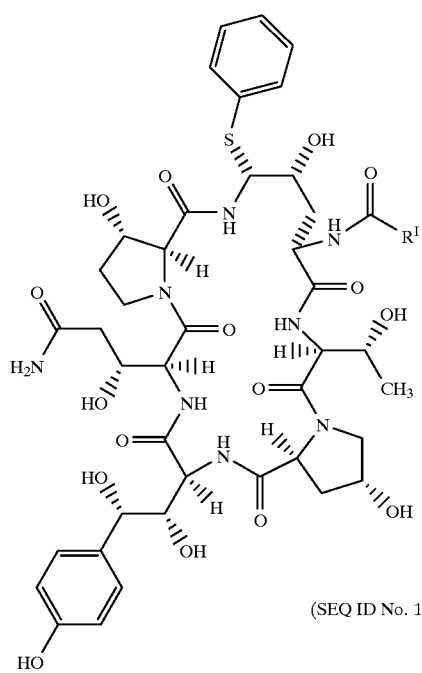
(VI)
(SEQ ID No. 1)

b) subsequently reacting Compound VI with phenylboronic acid, p-methoxyphenylboronic acid or methaneboronic acid to afford Compound IIIa of the formula:

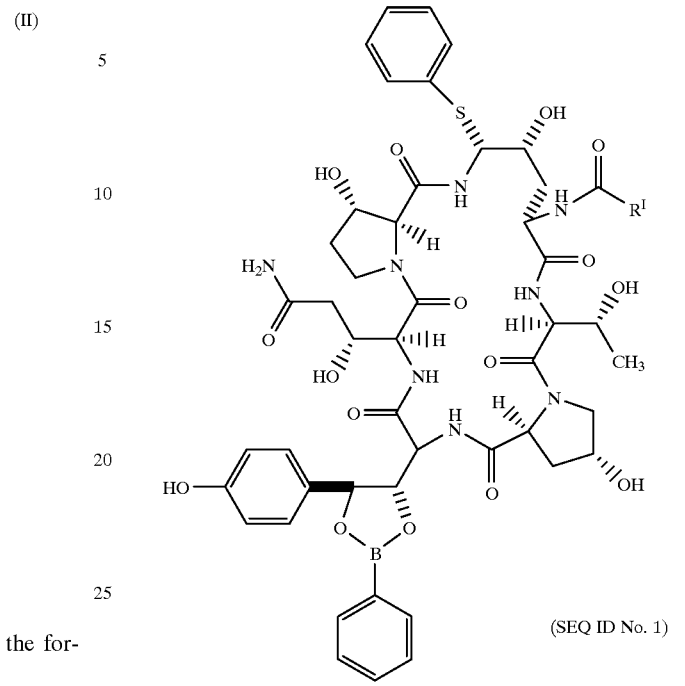
(IIIa)
(SEQ ID No. 1)

c) which is subsequently reduced and hydrolyzed to afford Compound V of the formula:

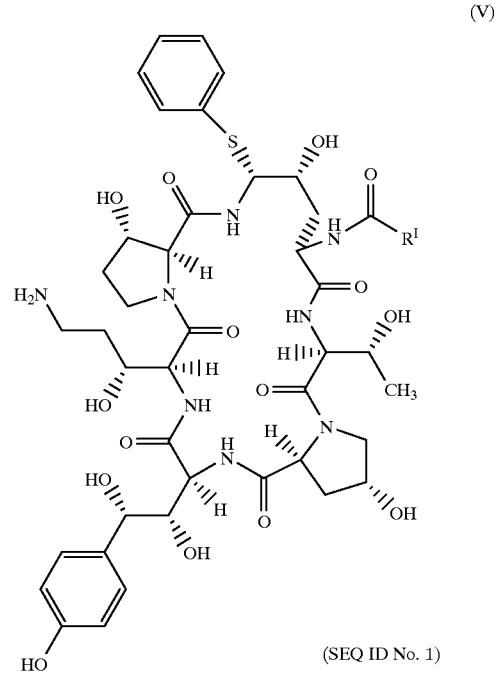
(V)
(SEQ ID No. 1)

d) which is stereoselectively converted to Compound I of the formula

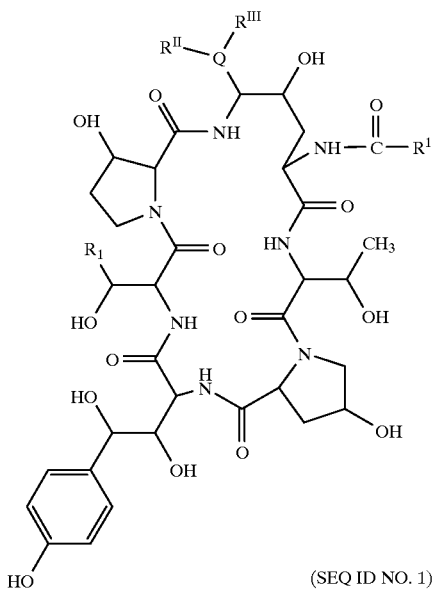

(I)

(SEQ ID NO. 1)

by the displacement of the phenylthio group.

8. The process of claim 7 wherein the reduction in Step (c) is accomplished using a borane complex or metal boride.

9. The process of claim 8 wherein the metal boride is $ZrCl_4/NaBH_4$ or $TiCl_4/NaBH_4$ and the borane complex is borane complexed with dimethylsulfide, dibenzylsulfide, diphenylsulfide, THF or 1,4-oxathiane or $BH_2Cl$ with dimethylsulfide.

10. The process of claim 7 wherein Compound II is converted to the phenylsulfide by reaction with thiophenol in a suitable solvent.

11. The process of claim 10 wherein the suitable solvent is acetonitrile.

12. The process of claim 7 where the displacement of the phenylthio group takes place in neat ethylenediamine or with ethylenediamine dissolved in a suitable solvent at a temperature of about 10° C. to about 40° C.

13. The process of claim 12 wherein the suitable solvent is selected from the group consisting of water, methanol, ethanol, tetrahydrofuran, isopropanol, trifluoroethanol, acetonitrile and dichloromethane.

14. A compound of the formula

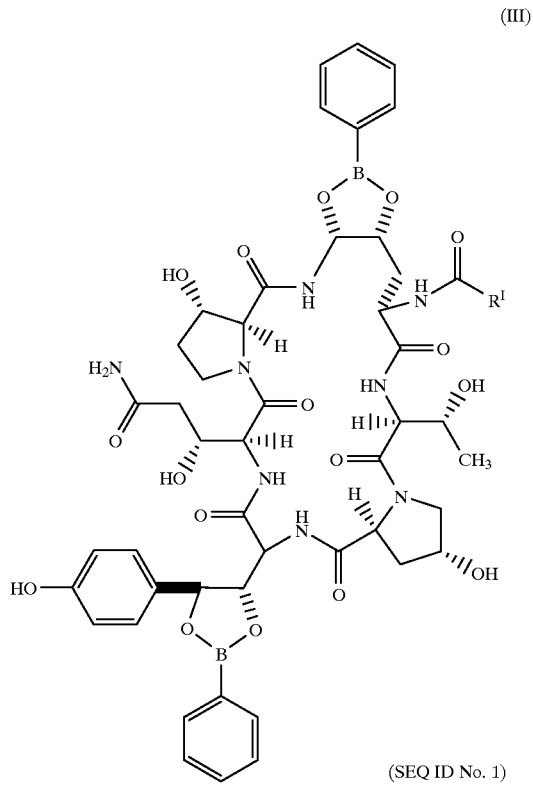

(III)

(SEQ ID No. 1)

wherein $R^I$ is $C_9$–$C_{21}$ alkyl, $C_9$–$C_{21}$ alkenyl, $C_1$–$C_{10}$ alkoxyphenyl, $C_1$–$C_{10}$ alkoxynaphthyl, or $C_1$–$C_{10}$ alkoxyterphenyl.

15. A compound of the formula
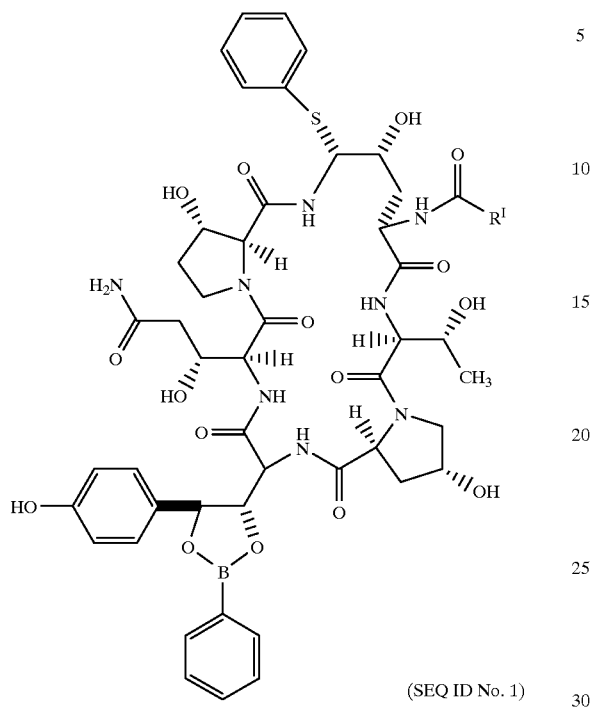
(IIIa)
(SEQ ID No. 1)
wherein
R$^I$ is C$_9$–C$_{21}$ alkyl,
C$_9$–C$_{21}$ alkenyl,
C$_1$–C$_{10}$ alkoxyphenyl,
C$_1$–C$_{10}$ alkoxynaphthyl, or
C$_1$–C$_{10}$ alkoxyterphenyl.
* * * * *

UNITED STATES PATENT AND TRADEMARK OFFICE
CERTIFICATE OF CORRECTION

PATENT NO. : 5,936,062
DATED : August 10, 1999
INVENTOR(S) : William Leonard and Kevin M. Belyk It is certified that error appears in the above-identified patent and that said Letters Patent is hereby corrected as shown below:

Claim 1, column 23, lines 1-27 should read as follows as per attached page.

Signed and Sealed this

Seventh Day of March, 2000

Attest:

Q. TODD DICKINSON

*Attesting Officer*  *Commissioner of Patents and Trademarks*

UNITED STATES PATENT AND TRADEMARK OFFICE
CERTIFICATE OF CORRECTION

PATENT NO.: 5,936,062
DATED: August 10, 1999
INVENTORS: William Leonard and Kevin M. Belyk It is certified that errors by the USPTO appear in the above-identified patent and that said Letters Patent is hereby corrected as shown below:

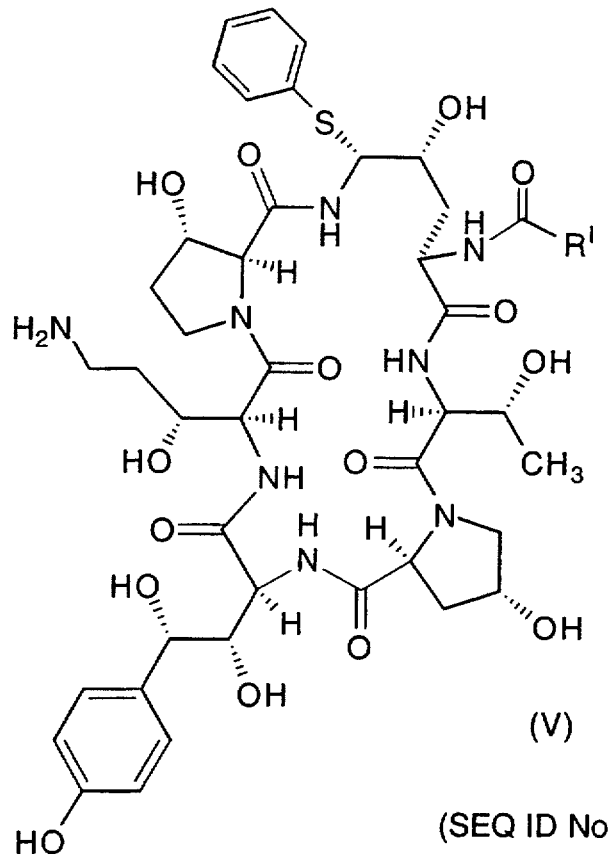

(V)

(SEQ ID No. 1)

UNITED STATES PATENT AND TRADEMARK OFFICE

CERTIFICATE OF CORRECTION

PATENT NO.: 5,936,062
DATED: August 10, 1999
INVENTORS: William Leonard and Kevin M. Belyk It is certified that errors by the USPTO appear in the above-identified patent and that said Letters Patent is hereby corrected as shown below:

At claim 1, column 23, lines 29-30 should read as follows:

d) which is stereoselectively converted to Compound I of the formula

At claim 7, column 24, lines 17-42 should read as follows

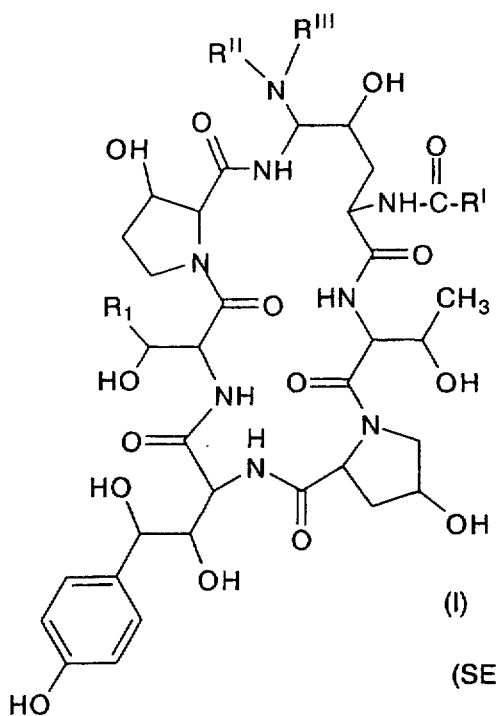

(I)

(SEQ ID No. 1)